(12) United States Patent
Lewis et al.

(10) Patent No.: US 10,130,403 B2
(45) Date of Patent: *Nov. 20, 2018

(54) SYSTEM FOR ACHIEVING SELECTABLE FIXATION IN AN ORTHOPEDIC PLATE

(71) Applicant: ORTHOHELIX SURGICAL DESIGNS, INC., Medina, OH (US)

(72) Inventors: Derek S. Lewis, Copley, OH (US); Andrew J. Leither, Akron, OH (US); Rebecca F. DiLiberto, Wadsworth, OH (US)

(73) Assignee: Orthohelix Surgical Designs, Inc., Medina, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/827,940

(22) Filed: Aug. 17, 2015

(65) Prior Publication Data
US 2015/0351816 A1 Dec. 10, 2015

Related U.S. Application Data

(62) Division of application No. 12/932,970, filed on Mar. 10, 2011, now Pat. No. 9,113,970.
(Continued)

(51) Int. Cl.
*A61B 17/80* (2006.01)
*A61B 17/86* (2006.01)
(Continued)

(52) U.S. Cl.
CPC ...... *A61B 17/8047* (2013.01); *A61B 17/1728* (2013.01); *A61B 17/8057* (2013.01);
(Continued)

(58) Field of Classification Search
CPC .................. A61B 17/8052; A61B 17/8047
See application file for complete search history.

(56) References Cited

U.S. PATENT DOCUMENTS

| 4,456,010 A | 6/1984 | Reimels et al. |
| 5,134,909 A | 8/1992 | Sasaki |

(Continued)

FOREIGN PATENT DOCUMENTS

| WO | 2004/096067 A1 | 11/2004 | |
| WO | WO2006103245 | * 5/2006 | ............. A61B 17/80 |

(Continued)

*Primary Examiner* — Samuel Hanna
(74) *Attorney, Agent, or Firm* — Duane Morris LLP

(57) ABSTRACT

An orthopedic plate and fastener system is provided for fixation of bones which has an implant that can selectably be used to achieve fixed angle and variable locking of the fasteners, as well as non-locking of the fasteners. The system includes a variable locking assembly that includes a locking insert, having threads which mates with internal threads of a through opening in the implant. The system also provides for locking fixed angle fixation, and non-locking variable angle fixation, all of which can be used with the threaded holes of the plates. The locking insert is provided on a ring driver, which is similar to or acts as the drill guide used with the locking fasteners of the present. Thus, the invention also relates to a method of enabling surgery where the surgeon can select the mode of fixation of fasteners between variable axis locking, variable axis non-locking, and fixed angle locking fixation, all utilizing the same fastener opening within the implant.

12 Claims, 8 Drawing Sheets

Related U.S. Application Data

(60) Provisional application No. 61/339,857, filed on Mar. 10, 2010.

(51) Int. Cl.
*A61B 17/17* (2006.01)
*A61B 17/88* (2006.01)

(52) U.S. Cl.
CPC ........ *A61B 17/861* (2013.01); *A61B 17/8888* (2013.01); *A61B 17/8615* (2013.01)

(56) References Cited

U.S. PATENT DOCUMENTS

| | | | |
|---|---|---|---|
| 5,531,746 A | 7/1996 | Errico et al. | |
| 5,876,402 A | 3/1999 | Errico et al. | |
| 5,954,722 A | 9/1999 | Bono | |
| 6,022,350 A | 2/2000 | Ganem | |
| 6,030,389 A | 2/2000 | Wagner et al. | |
| 6,206,881 B1 | 3/2001 | Frigg et al. | |
| 6,322,562 B1 | 11/2001 | Wolter | |
| 6,331,179 B1 | 12/2001 | Freid et al. | |
| 6,454,760 B2 | 9/2002 | Wagner et al. | |
| 6,485,520 B1 | 11/2002 | Hubach et al. | |
| 6,623,486 B1 | 9/2003 | Weaver et al. | |
| 6,679,883 B2 | 1/2004 | Hawkes et al. | |
| 6,902,567 B2 * | 6/2005 | Del Medico | A61B 17/746 411/271 |
| 6,955,677 B2 | 10/2005 | Dahners | |
| 6,964,664 B2 | 11/2005 | Freid et al. | |
| 7,052,499 B2 | 5/2006 | Steger | |
| 7,141,051 B2 | 11/2006 | Janowski et al. | |
| 7,175,624 B2 | 2/2007 | Konieczynski et al. | |
| 7,179,260 B2 | 2/2007 | Gerlach et al. | |
| 7,201,753 B2 | 4/2007 | Schlapfer et al. | |
| 7,229,443 B2 | 6/2007 | Eberlein et al. | |
| 7,325,470 B2 | 2/2008 | Steger et al. | |
| 7,914,561 B2 | 3/2011 | Konieczynski et al. | |
| 8,460,306 B2 | 6/2013 | Schaffran et al. | |
| 2002/0058939 A1 | 5/2002 | Wagner et al. | |
| 2002/0062127 A1 * | 5/2002 | Schumacher | A61B 17/8047 606/70 |
| 2002/0128654 A1 * | 9/2002 | Steger | A61B 17/8047 606/291 |
| 2004/0073218 A1 | 4/2004 | Dahners | |
| 2004/0153073 A1 | 8/2004 | Orbay | |
| 2005/0033298 A1 | 2/2005 | Hawkes et al. | |
| 2005/0080421 A1 | 4/2005 | Weaver et al. | |
| 2005/0143742 A1 | 6/2005 | Porcher | |
| 2005/0149040 A1 | 7/2005 | Haines et al. | |
| 2005/0277937 A1 | 12/2005 | Leung et al. | |
| 2006/0106398 A1 | 5/2006 | Lauryssen et al. | |
| 2006/0116678 A1 * | 6/2006 | Impellizzeri | A61B 17/8057 606/291 |
| 2006/0149265 A1 * | 7/2006 | James | A61B 17/8057 606/281 |
| 2006/0189990 A1 | 8/2006 | Farris et al. | |
| 2006/0200148 A1 | 9/2006 | Matthys | |
| 2006/0235400 A1 | 10/2006 | Schneider | |
| 2006/0241618 A1 | 10/2006 | Gasser et al. | |
| 2007/0083207 A1 | 4/2007 | Ziolo et al. | |
| 2007/0088360 A1 | 4/2007 | Orbay et al. | |
| 2007/0162016 A1 | 7/2007 | Matityahu | |
| 2007/0162147 A1 | 7/2007 | Lewis et al. | |
| 2007/0233116 A1 | 10/2007 | Olerud | |
| 2008/0009870 A1 | 1/2008 | Lombardo et al. | |
| 2008/0058817 A1 | 3/2008 | Eberlein et al. | |
| 2008/0114359 A1 | 5/2008 | Murner et al. | |
| 2008/0119895 A1 | 5/2008 | Manceau | |
| 2008/0234677 A1 | 9/2008 | Dahners et al. | |
| 2008/0234749 A1 * | 9/2008 | Forstein | A61B 17/8057 606/291 |
| 2008/0306550 A1 | 12/2008 | Matityahu | |
| 2009/0018557 A1 | 1/2009 | Pisharodi | |
| 2009/0018588 A1 | 1/2009 | Eckhof et al. | |
| 2009/0036932 A1 | 2/2009 | Rouyer et al. | |
| 2009/0048605 A1 * | 2/2009 | Yurek | A61B 17/8052 606/104 |
| 2009/0192549 A1 | 7/2009 | Sanders | |
| 2009/0248087 A1 | 10/2009 | Lewis et al. | |
| 2009/0292318 A1 | 11/2009 | White et al. | |
| 2009/0299369 A1 | 12/2009 | Orbay et al. | |
| 2009/0312803 A1 * | 12/2009 | Austin | A61B 17/8014 606/305 |
| 2010/0030277 A1 | 2/2010 | Haidukewych et al. | |
| 2010/0057138 A1 | 3/2010 | Murner et al. | |
| 2010/0069969 A1 | 3/2010 | Ampuero et al. | |
| 2010/0082070 A1 | 4/2010 | Diez | |
| 2011/0098754 A1 * | 4/2011 | Hulliger | A61B 17/8047 606/305 |

FOREIGN PATENT DOCUMENTS

| | | | |
|---|---|---|---|
| WO | 2006/102110 A1 | 9/2006 | |
| WO | WO2006102110 * | 9/2006 | ............ A61B 17/80 |
| WO | 2006/103245 A1 | 10/2006 | |
| WO | WO2010138260 * | 2/2010 | ............ A61B 17/80 |

* cited by examiner

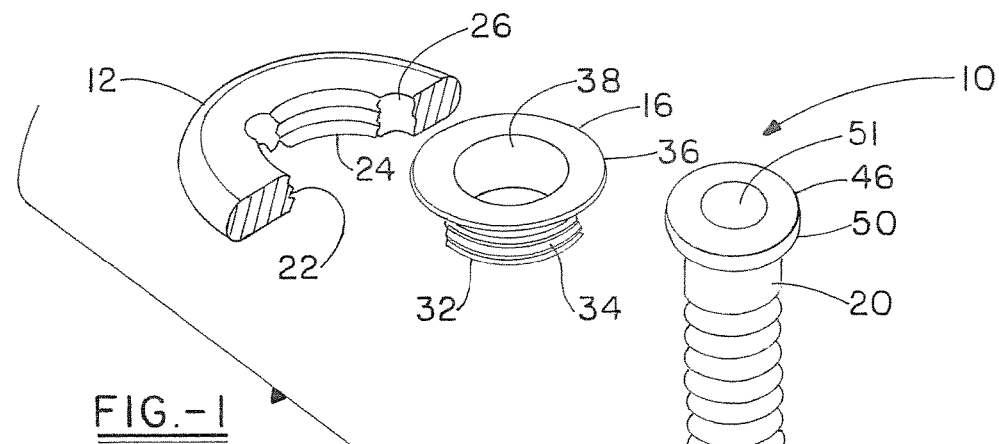
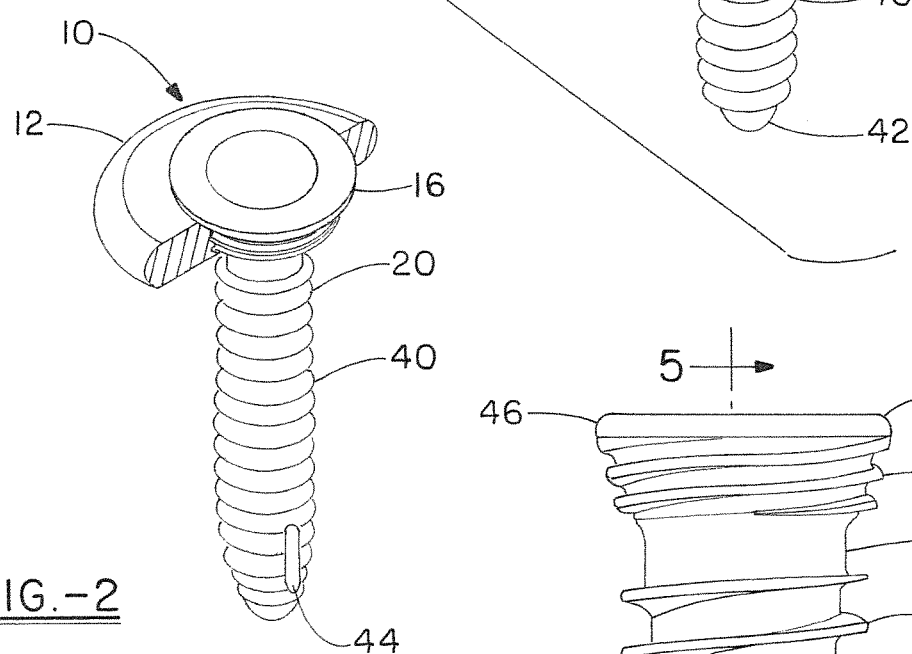
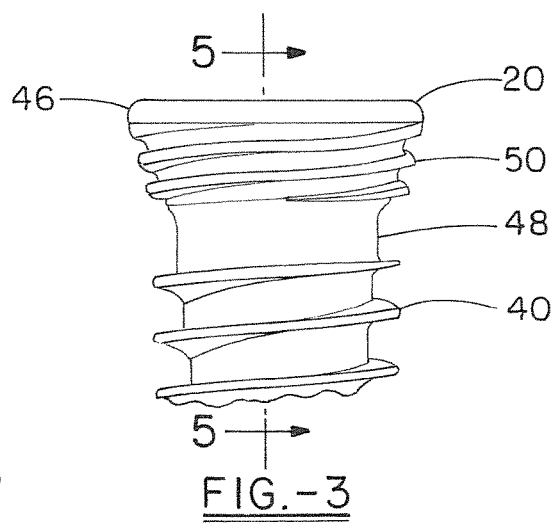
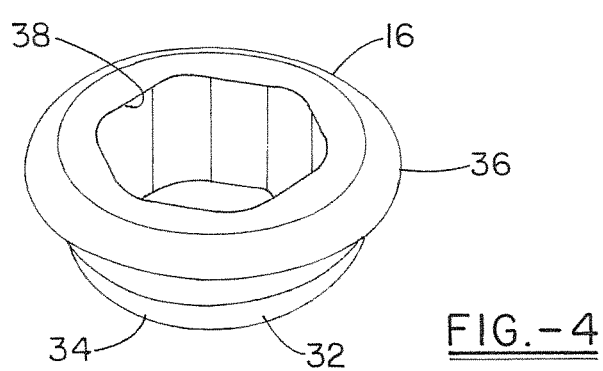

SYSTEM FOR ACHIEVING SELECTABLE FIXATION IN AN ORTHOPEDIC PLATE

CROSS-REFERENCE

This Application is a divisional application of U.S. application Ser. No. 12/932,970, filed on Mar. 10, 2011, which claims the benefit of priority under 35 U.S.C. § 119 of U.S. Provisional Application Ser. No. 61/339,857, filed on Mar. 10, 2010, herein fully incorporated by reference.

FIELD OF THE INVENTION

The present invention relates to an orthopedic plate and fastener system for fixation of bone, and further in particular to an orthopedic plate and fastener system which can selectably be used without substantial modification to surgical procedure to achieve fixed angle and variable locking of the fasteners, as well as variable angle non-locking of the fasteners, all within the same fastener opening of the plate.

BACKGROUND OF THE INVENTION

The use of ORIF (Open Reduction, Internal Fixation) has become a mainstay in the treatment of a variety of medical conditions. The corresponding design of orthopedic implants used to achieve this fixation has progressed through the development of plates or other stabilization means, including for example rods and or mesh, intended for application to specific bones, and for use with characteristic types of medical conditions. These plates are optimally designed to correspond to a generalized shape of the bone. The systems that use these plates include fixation means or fasteners, which are usually screws or pegs, that hold the plate to the bone, and further hold fragments of the bone to the plate in association with other fragments so that the fragments will fuse together.

In position on the bone, the plate, fasteners and bone form a "construct" that accepts dynamic loading. The interaction of the fasteners, which are typically screws or pegs, with the bone, and with the plate is a complex matter. Typically, screws include a threaded shaft and pegs may include a threaded shaft or may simply be cylindrical and be devoid of threads about the shaft. Bone has a hard cortical surface and a porous cancellous internal portion and the variable nature of bone must be taken into consideration in the design of an implant system. Further, as bone lives, it reacts to loading and to motion of the fasteners so that threads can loose purchase over time as the bone shifts away from the threads. Further loading between fragments influences fusion of the fragments. Thus, the design of the plate/fastener interface includes considerations of loading as well as accommodation of typical patterns of fragmentation and the intention to capture cortical surfaces and to avoid surrounding soft tissue.

The use of fixation plates generally falls into two categories, the repair of fractures and the reconstruction of degenerative bone pathology. Over time, the sophistication of the implants used to treat these conditions has increased dramatically. Initially, a fixation plate and its associated fasteners were not mechanically fixed to one another. In these early plate and fastener systems the trajectory of the fastener tended to be defined by the trajectory of the fastener hole with in the plate since this would be used to guide the fastener, or drill guide to form the fastener hole within the bone. In this type of fixation, the fasteners pass though the plate and into the bone. Fixation in this type of system is achieved by friction between the bone and the plate/fastener construct, and the construct is referred to as having "non-locking" fixation.

In contrast, fixation plates have developed in which the fasteners are mechanically locked at a predetermined and fixed angle relative to the plate, often through the use of a fastener having a threaded head which mates with internal threads in the fastener holes of the plate. This type of fixation is referred to as "locking fixation." Locking fasteners have the advantage of being less likely to back out of the plate, or to provide proud surfaces that can result in irritation to surrounding soft tissue. Moreover, in locking plate systems, the angle of the fastener axis relative to the plate, and the length of the screw is determined to account for capture of bone fragments for typical injury or deformation. In some ways this makes the surgeon's job easier in deciding on fastener placement. Often in this mode of fixation, a drill guide is used in conjunction with the fastener hole to drill the fastener hole within the bone.

In the locking plate construct, fixation strength does not rely on the bone and plate interaction. This facilitates the creating of a "bridge" construct that was once only possible by using a large external frame. The majority of internal fixation plates used today are the locking variety. This type of plate is especially useful in patients with low density bone, often the elderly or diabetic, where the necessary screw purchase for a non-locking construct is not present. While these types of plates, known as "locking plates", have become the standard of care in both reconstructive and trauma plating, there is evidence within the medical community, that there are some potential problems with overly stiff locking constructs. There is growing evidence that some locking constructs have become too stiff to allow for proper bone healing. There is evidence that non-union rates trend higher with extremely rigid stainless steel locking plates when compared to more flexible titanium plates. There have been published studies that suggest that a less rigid but strong construct may be optimal to provide stability while not interfering with the normal fracture healing mechanics and physiology.

"Variable angle" locking technology, often described as "poly-axial", refers to the ability to choose the angle of the fastener axis relative to the fastener hole within the plate and to lock the fastener at that angle in the plate. This mode of fixation provides the surgeon with the ability to create a rigid construct while allowing the flexibility to place the fixation screws at the optimal trajectory. In this type of fixation, the angle is determined through the use of a drill guide, which sets the angle in the bone. Current solutions on the market do provide the ability to vary the angle of the locking screws, but they do so by significantly compromising the strength of the interaction between the plate and the screw. This creates a greatly weakened overall construct when compared to a traditional fixed angle locking construct. Additionally, the current variable angle locking designs modify both the plate and screw in every, non-compression, hole within the plate. This leaves all of the plate holes compromised even if the nominal angle of the screw hole would have been appropriate.

The present invention addresses the weaknesses of the systems currently on the market. It increases the strength of the variable angle locking mechanism so as to make it more clinically effective. Further, increasing the strength reduces the chance of construct failure and resultant non-union of the fixed bones. This has serious consequences for both the surgeon and the patient being treated. A stronger mechanism will also allow the technology to be deployed beyond the current scope of the prior art products due to this inherent relative weakness. Additionally, initial testing of the present variable locking mechanism demonstrates that the system provides fixation that is stronger but less rigid and the current literature suggests that this may provide a significantly positive impact on fracture union rates.

The variable locking mechanism of the present invention can be used with existing threaded locking plates without change to the plates or the addition of steps to the surgical procedure. The present invention enables three modes of fixation within a single threaded hole, and does not even require any modification to present locking plates or any significant modification to the current surgical procedure used to achieve fixed angle locking. This is accomplished by installing a locking ring into the plate with an installation tool that resembles a traditional locking screw drill guide. This ring will be installed such as by a friction fit on the drill guide, and at the surgeon's discretion the ring driver is used in place of the traditional drill guide. In a further embodiment, the drill guide has a conical opening and a scalloped edge. The ability to add function to an existing system without adding steps or altering the typical flow of the surgical procedure is a critical user need for almost any surgical product and greatly enhances the acceptance and ease with which a new product is adopted.

The present invention also provides a variable angle non-locking fastener, which can similarly be used in the threaded locking holes of existing plates. Fasteners are provided within the same system (and in particular in the same surgical tray), which have a rounded smooth head that is sized to ride on the threads of the fastener hole so as to provide for a variable angle non-locking relationship with the plate. The drill guide is used to set the angle in the bone, which in turn sets the angle relative to the plate. Thus, the present invention provides the surgeon with three modes of fixation (locking fixed angle, locking variable angle and non-locking variable angle) using virtually the same plate, instruments and surgical procedure that the surgeon has become used to for fixed angle locking fixation. The present invention provides the surgeon with the ability in his or her discretion to select the mode of fixation in the operating room as the needs of the patient dictate. Without any significant change to inventory (the plate inventory remains the same, and the change is simply the addition of two types of screws, the locking inserts, the locking insert driver, and a drill guide for the non-locking screws.) The present invention allows the surgeon to decide once he has had a chance to view the open surgical site whether to utilize the strength of a fixed angle lock at a pre-selected angle or to alter the trajectory of the fastener the strength of the relation between the plate and the fastener.

The present invention can be used in any number of surgical applications, including for example, for any orthopedic implant application such as for example for craniofacial plates, trauma plates, small bone plates, long bone plates, and for the spine or pelvis.

SUMMARY OF THE INVENTION

The present invention provides a system of orthopedic plates and fasteners which provides for selectable fixation between three modes of fixation, i.e. fixed angle locking fixation, variable angle locking fixation, and non-locking fixation all within a single fastener opening. One aspect of the present invention includes a variable locking assembly that has a locking insert that is threaded into, and thus mechanically seated in, the internally threaded opening in an implant. The locking insert has an annular flange or shoulder that surrounds the opening in the implant on the superior surface, and also has a central through opening that is preferably smooth and hexagonal in cross section to allow the insert to be screwed into the plate opening. The locking insert is made from a biocompatible material that can be deformed by the threads of the fastener head, (i.e. a screw or peg,) so that the fixator is inserted through the locking insert and into the adjacent bone to the point where the proximal head threads interact with the internal opening of the locking insert to cause the material to flow and accept the head of the fastener at any angle (up to ~20°) while maintaining a rigid construct. Both the minor diameter and the major diameter of the screw head include a taper to improve the locking within the locking insert. Preferably, the major diameter of the threads taper out at a larger angle than the minor diameter, i.e. by a difference of from about 2° to about 20°, preferably from about 5° to about 15°, and preferably about 8° to about 12° degrees of difference so that the threads widen at a greater rate than the head does to improve the strength of the fixation when the fastener is locked into the insert. The invention further includes a tool for insertion of the locking insert into the plate. The insert can be provided on the tool, which has a friction fit, such as a tapered head split that compresses to hold the insert and allow the insert to be threaded into the screw hole of the plate. The tool is advantageously made of plastic, and is a single use device.

The present invention relates to a system of orthopedic plates that also provide for fixed angle locking using the same plate holes as for the variable angle locking. In this case, the fastener includes a threaded head that corresponds to the internal threads of the fastener hole in the plate. In this case, the fixed angle is defined by the angle of the hole in the plate, and the hole and the fastener are co-axial. The system also provides for variable angle non-locking. Thus, the system also includes fasteners that could be used in the same threaded plate holes to hold the plate relative to the bone, but which do not lock the plate to the fastener. Advantageously, these fasteners have convexly rounded heads that are sized to fit within the threaded hole at a variable angle providing for about 20° of conical rotation relative to the longitudinal axis of the fastener hole. Thus, the invention relates to a surgical tray or caddy that includes orthopedic plates which have internally threaded fastener holes, a variable locking insert which threads into the threaded fastener hole and which has a through opening and an externally threaded fastener that can be inserted into the locking insert to deform the surface of the through opening to lock the fastener at a selected angle relative to the fastener hole, and at least one of a fastener having a head with threads that are capable of mating with the threads of the fastener hole or a fastener that has a convexly rounded surface that is sized to fit with the fastener hole and hold the plate but also to allow for a variable angle position of the fastener within the fastener hole.

BRIEF DESCRIPTION OF THE DRAWINGS

FIG. 1 is an exploded view of a variable locking assembly in accordance with the present invention with the plate illustrated in section;

FIG. 2 is a view from the top and the side of the variable locking assembly of the present invention;

FIG. 3 is a side view of the screw head of FIG. 1;

FIG. 4 is a top side view of variable locking insert of FIG. 1;

DETAILED DESCRIPTION OF THE INVENTION

Figure 5:
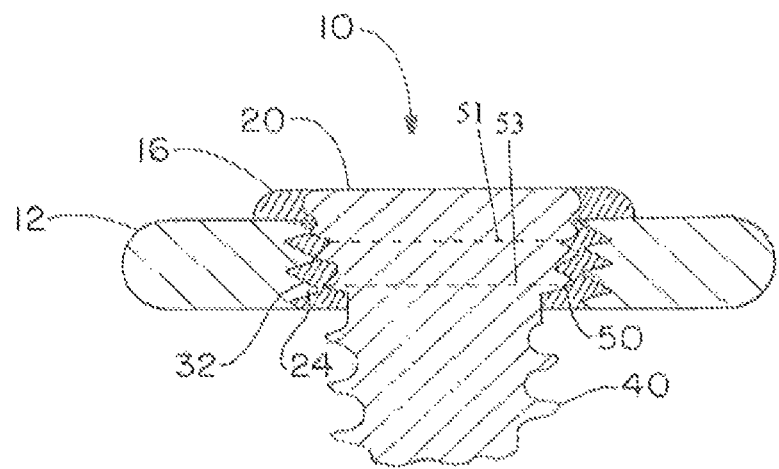
FIG. 5 is a cross section of the variable locking assembly insert of FIG. 2 taken along line 5-5.
Figure 7:
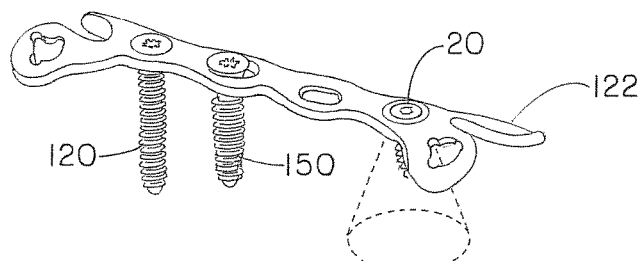
FIG. 7 is a top side view of a bone plate and fastener system illustrating the use of all three modes of fixation provided by the present invention.
Figure 8:
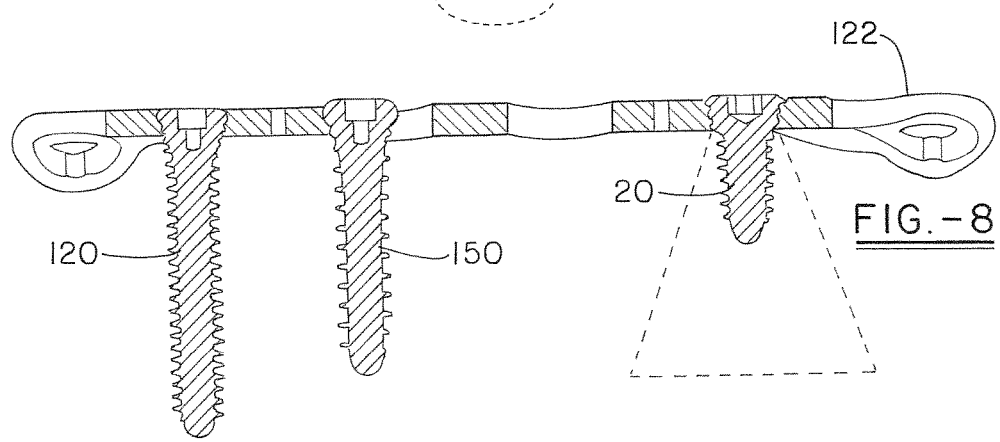
FIG. 8 is a cross-section of the bone plate of FIG. 7 taken along line 8-8.
Figure 9:
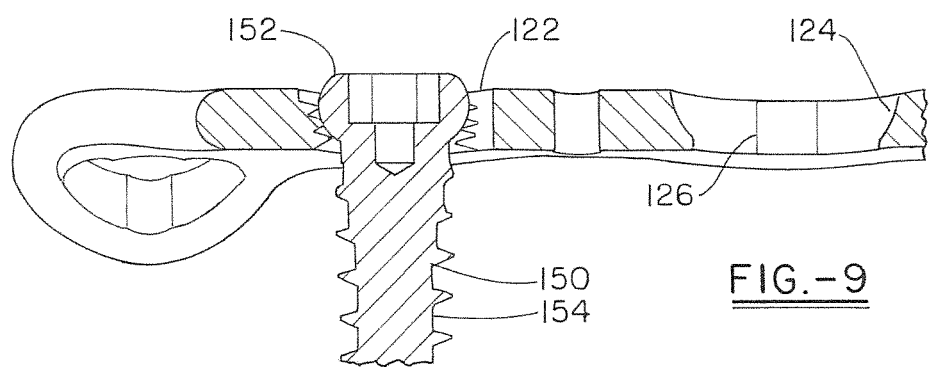
FIG. 9 is view of the variable non-locking fixation of the present invention taken from the same cross-sectional view as for FIG. 8.

FIG. 1 shows an exploded view of a variable axis locking mechanism assembly in accordance with the present invention that is further illustrated in FIGS. 2 through 5. FIG. 5 shows a cross section of the assembly of FIG. 1. The assembly 10 includes an implant member that is shown as a plate 12, a locking insert 16 and a variable locking fastener, which is shown as a screw 20. For the purpose of this description, the plate is shown in FIGS. 1, 2, 5, and 6 as part of an annular portion of a plate including a through hole 22 with internal threads 24, and optionally grooves 26 that act as seats for a drill guide. The plate could have any appropriate shape according to the application with which it is used, distal radius plates, calcaneal plates, long bone plates, plates for the clavicles, spinal plates, plates for use in the hand and foot, or any other surgical implant and accordingly is illustrated in FIGS. 7-9 as having a modified X-shape where the plate has diagonally opposed pairs of long and short arms that each include a threaded fastener hole. The plate is further shown as including one or more compression holes in the middle of the plate.

The plate generally has a top side, or side which faces away from the bone in use, with a generally constant through thickness to a bottom side, or side that faces toward the bone in use. The plate can be planar, or have another topography, according to the application, although the through hole portion 22 must have a topography that allows the through hole of being capable of receiving the locking insert 16 and the threads 24 of the hole are capable of mating with the external threads 32 of the body 34 of the locking insert or the head of a fastener designed for fixed angle locking (or alternatively of mating with the external threads 132 on the head 134 of a locking screw 120.) As illustrated in FIG. 4, the locking insert includes an annular flange member 36, which generally forms a shoulder area that seats against the top portion of the plate that surrounds the through hole 22. The locking insert further includes an internal opening 38 that is advantageously smooth and which has a cross-sectional configuration that allows the locking insert to be screwed into the plate hole. Preferably, this is a hexagonal shape having internal edges where the flats join that are smoothed out to better accommodate the screw head.

The locking insert is made from a biocompatible material such as PEEK polymer (i.e., polyether ether ketone) or other suitable biocompatible polymer, that is softer than the screw so that when the screw head is screwed into the locking insert, the external threads will cause the surface of the internal opening 38 to flow or deform to form threads in the locking insert, causing the screw to lock into position relative to the plate in the locking insert. Also advantageously, the locking insert 16 is provided in the surgical tray pre-mounted on a locking insert driver tool 160 shown in FIGS. 10-12. The tool 160 is similar in shape to the drill guide that is used with the system, and comprises a long hollow tube having a cannula which can receive and guide a guide for the drill used for the fastener that is used with the locking insert. The outside of the distal end of the tube fits into the through hole 22 of the locking insert 16 and is shaped such as in a hex shape corresponding to the shape of the internal opening 38 of the insert and tapered so as to be sufficiently secure to permit the tool to be used to drive the insert 16 into the plate 12.

Figure 22:
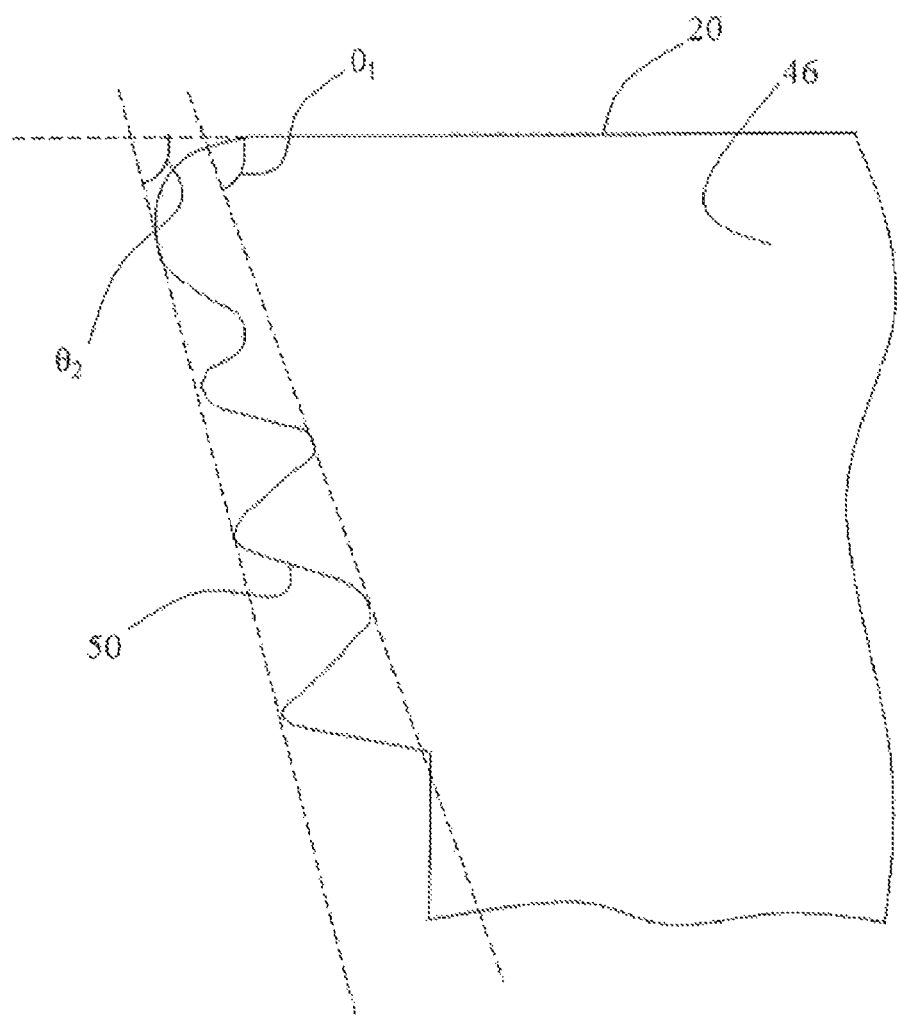
FIG. 22 is a detailed cross-section view of the variable locking fastener of FIG. 5.

FIGS. 1, 2 and 3 show a variable axis locking fastener which is shown as a screw 20; however, it should be understood that a peg could also be used. The screw includes a portion having a thread 40 for attachment within a bone or bone segment. The screw can include an insertion tip 42 that has a point, or as shown, a blunt tip with optional cutting flutes 44. The screw has a head portion 46 that is joined to the distal threaded portion by an area 48 having threads of a smaller major diameter and also including an area that is free from threads or is cylindrical. The head of the screw includes external threads 50 where the minor diameter 51 and major diameter 53 both taper, but preferably, the major diameter 53 tapers at a larger angle (relative to the proximal end of the screw) than the minor diameter 51 so that the threads become thicker as they progress toward the top end of the screw. As shown in FIG. 22, the minor diameter 51 tapers at an angle $\theta_1$ of from about 20° to about 60°, and preferably from about 30° to about 50° degrees and most preferably about 35° to about 45° while the major diameter 53 tapers at an angle $\theta_2$ of from about 30° to about 70°, and preferably from about 40° to about 60° degrees and most preferably about 45° to about 55° with an advantageous differential being about 8° to about 12°. The head portion 46 further includes a torque driving recess 52; with an optional bore 80 that retains the screw 20 on the post of a screwdriver. The variable locking assembly of the present invention allows a conical range of fixation of about 10° to about 25°, and preferably about 12° to about 22°, and more preferably about 15° to about 20°.

Figure 6:
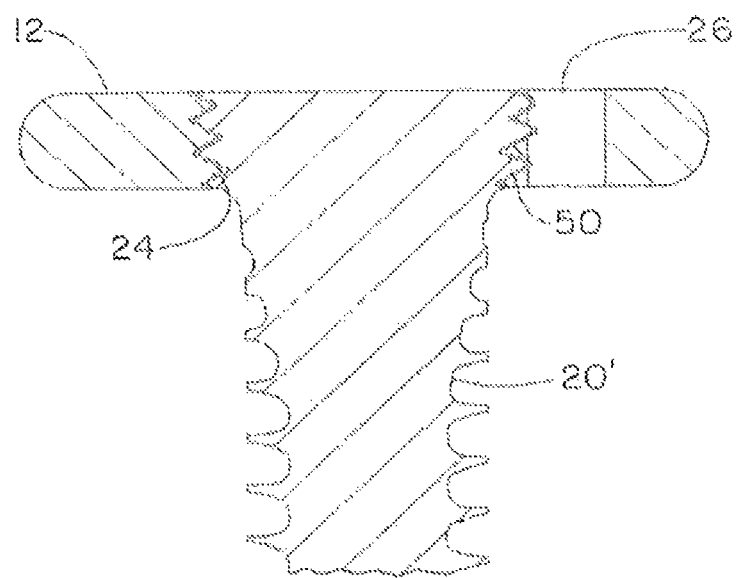
FIG. 6 is a cross section of the plate shown in FIG. 1 with a threaded locking screw.

FIG. 6 illustrates the plate 12 of the present invention accepting a locking screw 120 which has threads 132 on the exterior surface of the head 134 that mate with the through screws 24 of the through hole 22 in the plate. The distal portion of the locking screw corresponds to the distal threaded portion of the variable locking screw described above.

Figures 13, 14, 15:
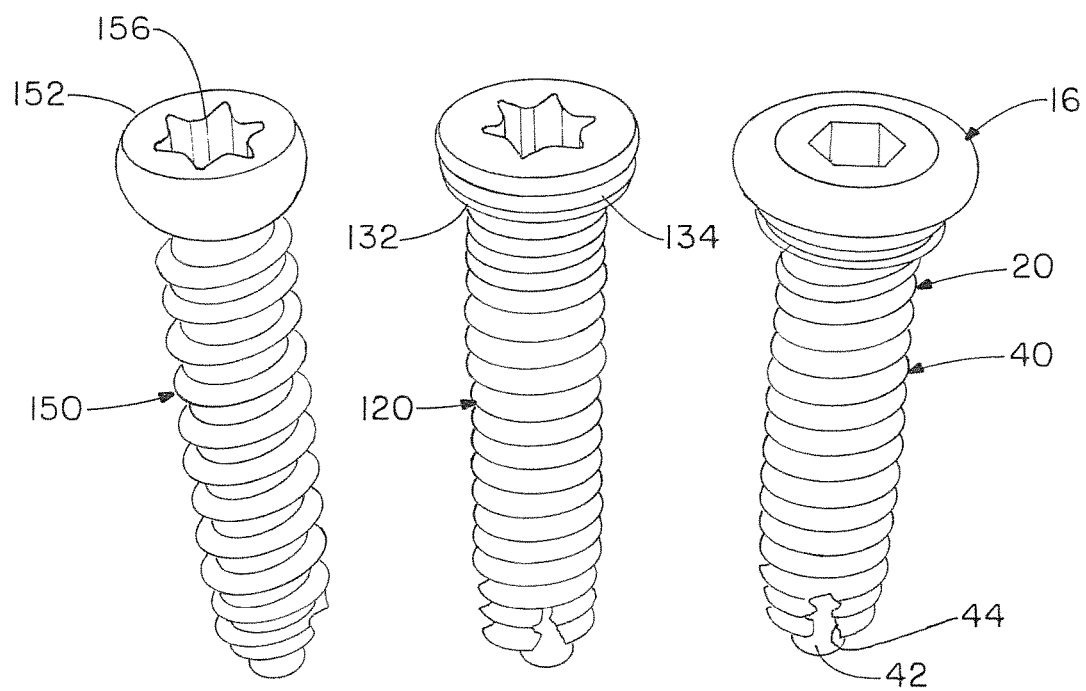
FIG. 13 is top side view of the variable angle non-locking screw of the present invention.
FIG. 14 is top side view of the fixed angle locking screw of the present invention.
FIG. 15 is top side view of the variable angle locking screw assembly of the present invention.
Figure 16:
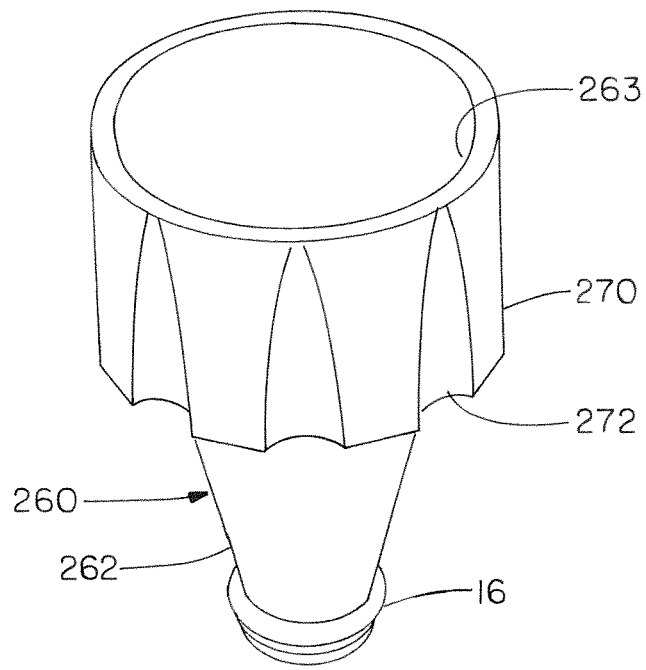
FIG. 16 is a side perspective view of the locking insert on a second embodiment of the insertion tool/drill guide for the variable locking assembly of the present invention.
Figure 17:
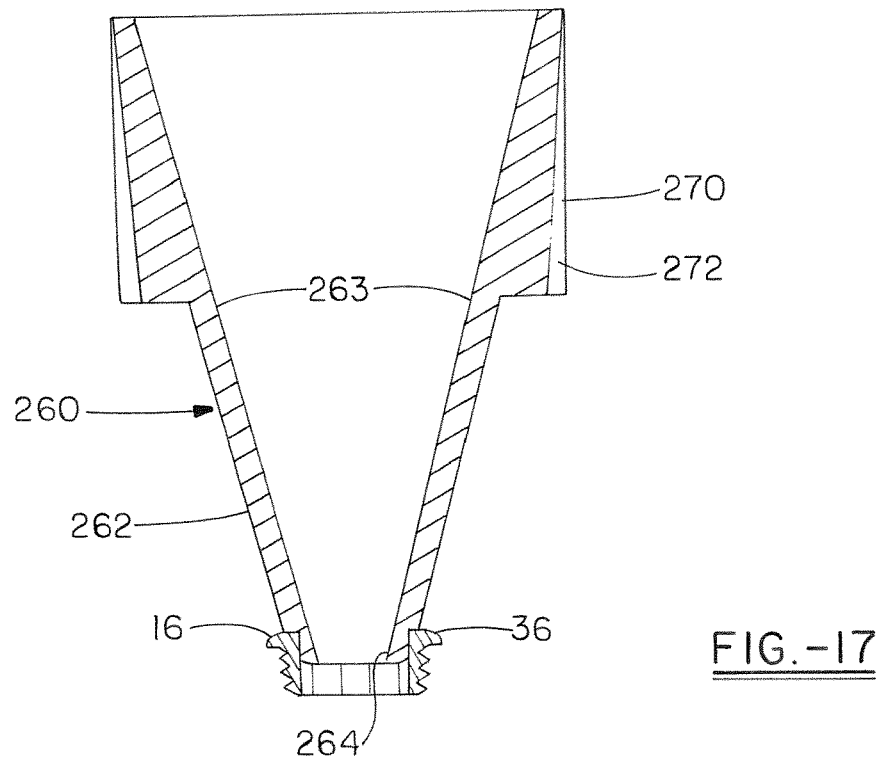
FIG. 17 is a side cross-sectional view of the drill guide/locking insert assembly of FIG. 16 taken along line 17-17 in FIG. 20.
Figure 18:
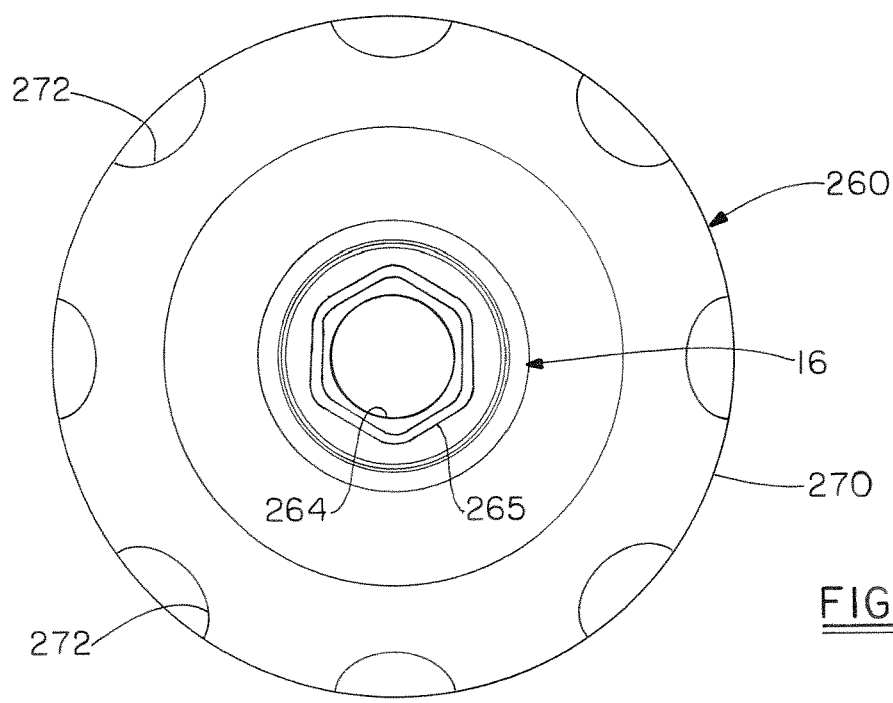
FIG. 18 is a bottom view of the drill guide/locking insert assembly of FIG. 16.

FIGS. 7-9 illustrate a modified X-shaped plate 122 that has threaded locking screw holes 122 and compression holes 124 that include a shoulder 126 to cause compression of the plate as the screw is driven down into the plate hole. This plate 12' is illustrated as including three modes of fixation, using a variable locking screw assembly 20, a threaded locking screw 120 and a non-locking variable screw 150. These three types of screws are better illustrated in FIGS. 13-15. FIG. 13 shows the non-locking screw 150 which has a rounded head 152 that rides on the internal threads of the fastener hole 22 within the plate as is shown in FIG. 9 in detail. Once again, the screw 150 further includes a torque driving recess 156 and bone threads which have a lower pitch then the other two types of screws provided with the present invention in order to provide better purchase in the bone. The screw has a head portion 152 that is convexly rounded, and preferably hemi-spherical, and sized so as to ride on the internal threads of the plate and to secure the plate to the bone, but to allow an conical range of fixation of about 10° to about 20°, and preferably about 12° to about 17°, and more preferably 15°, (which is lower than the angle permitted by the locking variable angle assembly since a higher angle contributes to lower strength. In order to compensate for the lower strength, the non-locking variable locking screw has a bone screw portion 154 that has a lower pitch and a slightly greater major diameter, with the same size minor diameter.

Figure 10:
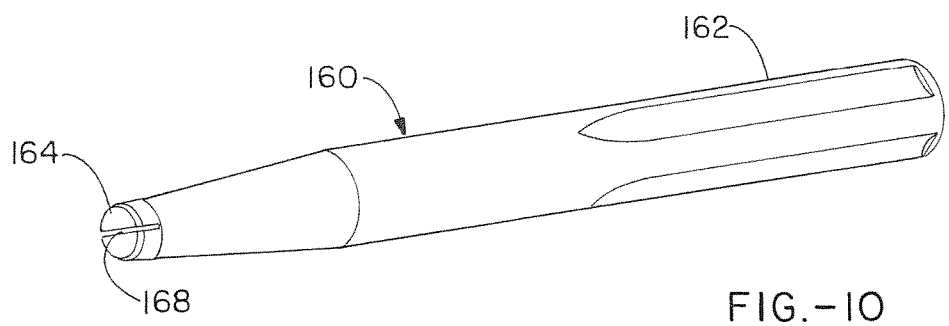
FIG. 10 is a top side view of the locking insert driver of the present invention.
Figure 11:
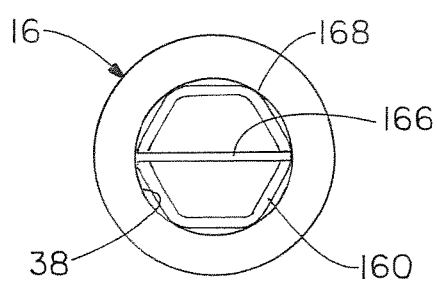
FIG. 11 is a distal end view of the locking insert on the insertion tool for the variable locking assembly of the present invention.
Figure 12:
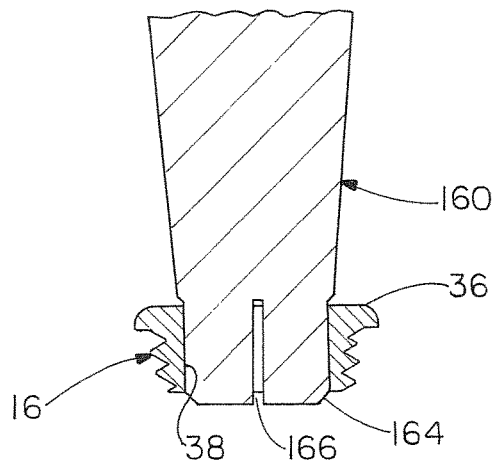
FIG. 12 is a cross-section distal end view of the locking insert on the insertion tool for the variable locking assembly of the present invention.

FIGS. 10-12 illustrate a locking insert driver 160 that can be used to install the insert in the plate of the present invention. The driver has a handle 162 and a tip 164 that includes a split 166 and ridges 168 which fit into radiused areas 37 within the locking ring insert through hole 38 in order to drive the insert into the through hole of the plate. The split allows the driver tip to compress to form a tighter friction fit of the insert on the driver.

Figure 19:
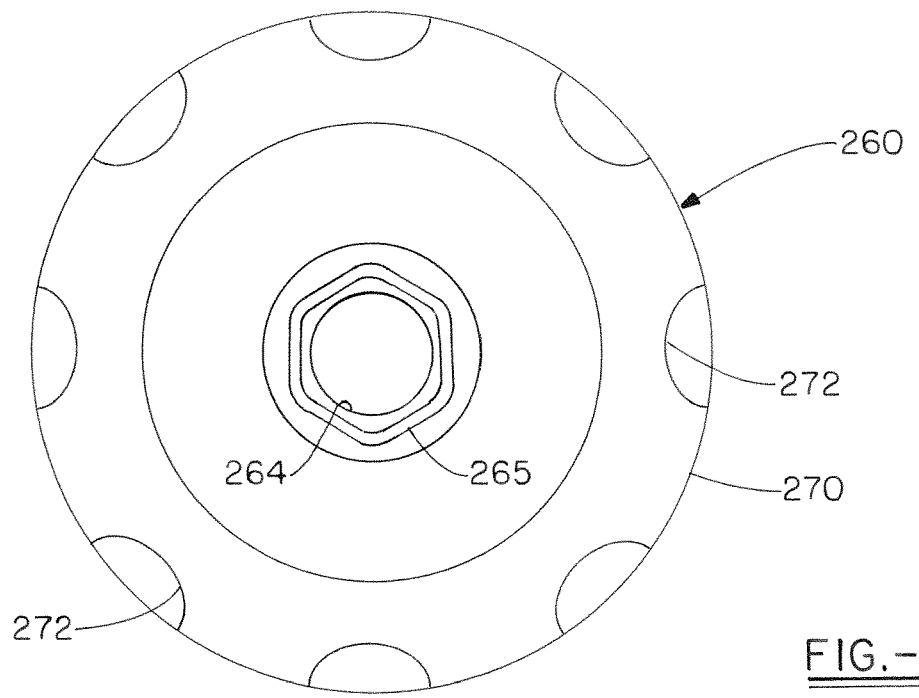
FIG. 19 is a bottom view of the drill guide of FIG. 16 without the locking insert.
Figure 20:
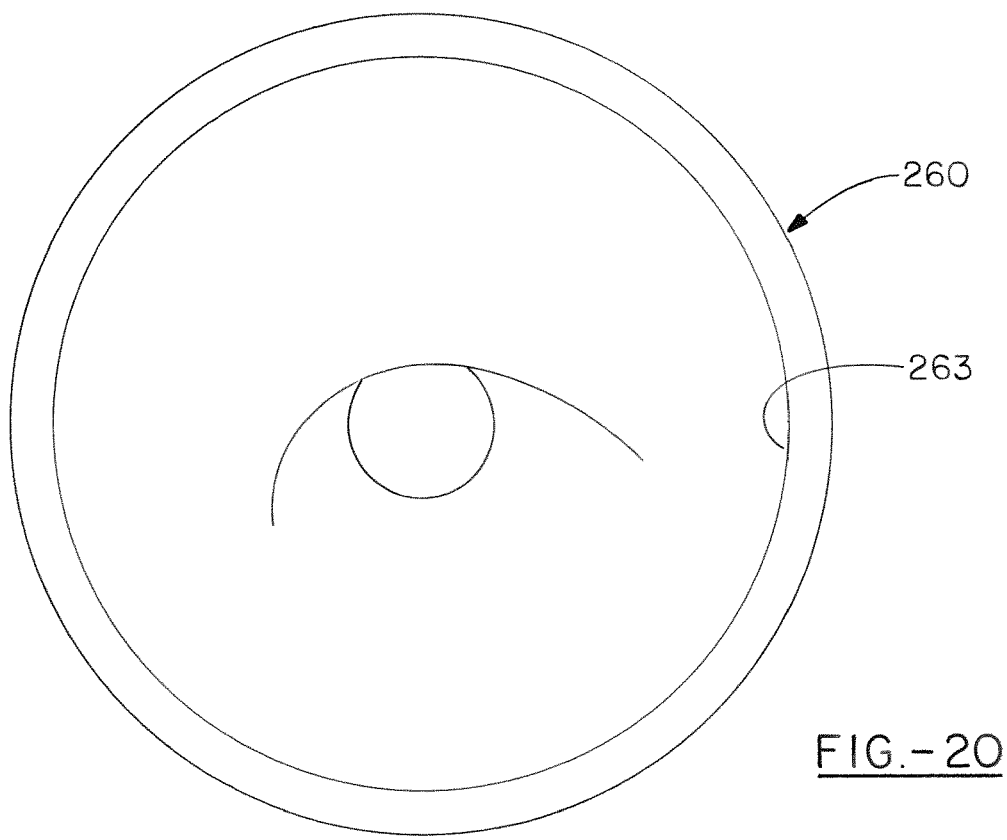
FIG. 20 is a top view of the drill guide of FIG. 16.
Figure 21:
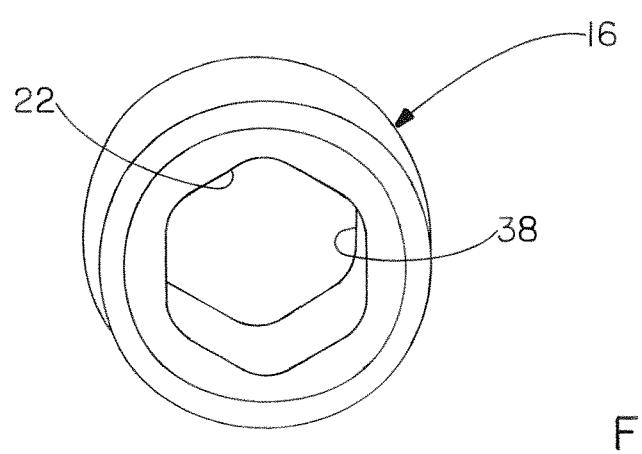
FIG. 21 is a top view of the locking insert.

FIGS. 16-20 illustrate a second embodiment of the locking insert driver 260 of the present invention. In this embodiment, the driver 260 is also useful as a poly-axial drill guide. Specifically, the driver has a conical shaped body portion 262, which functions both as a handle, and also provides a internal opening 263 that has conical shape that defines the limits that the variable locking screw can achieve in the plate. The internal opening 263 ends in a circular opening 264 through which the drill extends during use. On the external wall surrounding the opening 264 there is a tip 265 having friction fit with the locking insert 16. FIG. 21 illustrates a hexagonal shape 38 that the opening of the locking insert may have, and it should be understood that the tip has a corresponding shape as is shown in FIG. 19. Other forms of friction fit may be used so long as there is sufficient fit to allow the drill guide to be used to screw the locking insert into a screw hole in the plate. At the top end of the body portion 262 of the conical drill guide 260, the drill guide includes turn means 270 which allow a surgeon to thread the locking insert into the threaded screw hole of a plate using his or her fingers. It is preferred that the turn means 270 include a suitable configuration for this use, such as a polygonal shape, scallops as shown 272, or knurling, or cross-hatching.

The present invention is novel in providing a surgical caddy that includes a plate with threaded hole and a variable locking assembly that has a threaded deformable locking insert and a fastener having a threaded head that can be inserted in the locking insert to lock it into position, and either or both a locking fastener that has a threaded head that locks into the threaded hole to lock the fastener at a fixed angle, or a variable locking fastener that has a convexly rounded head that is sized to fit within the threaded hole so that the non-locking fastener can be inserted at a variable angle, but which secures the plate to the bone, but is not mechanically coupled to the plate. Thus, the surgeon is provided with a single plate, basically a single surgical procedure with very little change to provide selectable fixation by choosing the fastener.

Testing was performed on the variable locking mechanism of the present invention showing cyclic loading of the variable locking assembly of the present invention at an applied load of 35, 55, and 67.5 Newtons at a run cycle to failure or one million cycles. Only one of the assemblies of the present invention failed below the test end, i.e. at more than 300,000 cycles, while the majority of the comparative product failed at an average of 22,000 with loading at 55 N. The test results are shown below in Table 1.

TABLE 1

| Customer Spec ID | % Static Peak Load | Applied Load (N) | Applied Moment (N-m) | Cycles Tested (n) | Dynamic Stiffness (N/mm) | Observations and/or Failure mode |
|---|---|---|---|---|---|---|
| Stryker 15° | Cust P | 67.50 | 0.7425 | 71,102 | 22.92 | a |
| Stryker 15° | Cust P | 35.00 | 0.385 | 1,000,000 | 78.75 | b |
| Stryker 15° | Cust P | 55.00 | 0.605 | 30,530 | 70.71 | a |
| Stryker 15° | Cust P | 55.00 | 0.605 | 29,596 | 78.57 | a |
| Stryker 15° | Cust P | 55.00 | 0.605 | 44,539 | 99.00 | c |
| Stryker 0° | Cust P | 55.00 | 0.605 | 7,790 | 47.60 | c |
| Stryker 0° | Cust P | 55.00 | 0.605 | 15,472 | 58.24 | c |
| Stryker 0° | Cust P | 55.00 | 0.605 | 3,291 | 55.62 | c |
| Ortho 15° | Cust P | 55.00 | 0.605 | 1,000,000 | 88.39 | b |
| Ortho 15° | Cust P | 55.00 | 0.605 | 1,000,000 | 86.84 | b |
| Ortho 15° | Cust P | 55.00 | 0.605 | 317,842 | 88.39 | d |
| Ortho 0° | Cust P | 55.00 | 0.605 | 1,000,000 | 93.40 | b |
| Ortho 0° | Cust P | 55.00 | 0.605 | 1,000,000 | 90.00 | b |
| Ortho 0° | Cust P | 55.00 | 0.605 | 1,000,000 | 85.34 | b | a 2 mm of displacement, screw head pulled through plate, plate fracture
b no observed failure
c partial fracture of plate
d partial separation of peek ring from plate While in accordance with the patent statutes the best mode and preferred embodiment have been set forth, the scope of the invention is not limited thereto, but rather by the scope of the attached claims.

What is claimed is:

1. A variable angle locking mechanism assembly for use in an orthopedic implant in bone, the orthopedic implant including a through opening having a longitudinal axis and defining an internal wall with threads, the variable angle locking mechanism comprising:
   a locking insert having a body including external threads configured to mate with the threads of the through opening of the orthopedic implant, wherein the locking insert defines a fastener through hole that is further defined by an inner wall including longitudinal flat surfaces, wherein the locking insert further includes an annular flange extending radially outwardly about the through opening to form a shoulder that has an outer diameter greater than an outer diameter of said body, and is capable of mating against an external surface of the orthopedic implant; and
   a fastener having a first portion for attachment in bone having a first thread and a head portion having external threads, wherein the first portion defines a fastener axis and a minor diameter and a major diameter of the external threads are tapered relative to the fastener axis, and wherein the major diameter tapers at a larger angle with respect to a proximal end of the fastener than the minor diameter tapers with respect to the proximal end of the fastener, wherein the flat surfaces of the locking insert comprise a material configured to deform relative to a material of the external threads of the head portion of the fastener to form internal threads in the locking insert as the fastener is inserted into the locking insert such that the fastener head is coupled to the locking insert in a locked relation to the implant by threads formed in the inner wall.

2. The variable angle locking mechanism assembly as set forth in claim 1, wherein the orthopedic implant is a plate and the through opening in the plate can selectably accommodate either a fixed angle locking screw having a head with external threads that are capable of mating with the threads of the through opening of the plate or the locking insert.

3. The variable angle locking mechanism as set forth in claim 1, wherein the locking insert is made of PEEK polymer and the fastener is made of a metal.

4. The variable angle locking mechanism assembly as set forth in claim 3, wherein the fastener hole in the locking insert forms a torque driving recess.

5. The variable angle locking mechanism assembly as set forth in claim 1, wherein the fastener hole in the locking insert has a cross-section that forms a polygon having from 4 to 10 sides.

6. The variable angle locking mechanism assembly as set forth in claim 1, wherein the fastener hole of the locking insert is configured to receive a driver therein.

7. The variable angle locking mechanism assembly as set forth in claim 1, wherein the difference in the taper angle of the major diameter to the minor diameter is from about 5° to about 15°.

8. The variable angle locking mechanism assembly as set forth in claim 6, wherein the driver comprises a drill guide.

9. The variable locking mechanism assembly as set forth in claim 8 wherein the driver comprises a conical opening.

10. The variable angle locking mechanism assembly as set forth in claim 9, wherein the conical opening defines a limit of an angle of the fastener when inserted in the orthopedic implant.

11. The orthopedic plate system of claim 1, wherein the inner wall of the fastener hole is smooth.

12. The orthopedic plate system of claim 11, wherein the fastener hole has a hexagonal cross-section.

* * * * *